United States Patent [19]
Bell

[11] Patent Number: 5,947,729
[45] Date of Patent: Sep. 7, 1999

[54] MODULAR DENTAL SYSTEM AND METHODS

[75] Inventor: Daniel D. Bell, Littleton, Colo.

[73] Assignee: Bell Dental Products, LLC, Englewood, Colo.

[21] Appl. No.: 09/167,823

[22] Filed: Oct. 7, 1998

Related U.S. Application Data

[60] Provisional application No. 60/061,369, Oct. 8, 1997.

[51] Int. Cl.⁶ .................................................. A61C 1/02
[52] U.S. Cl. .................................................. 433/98; 433/27
[58] Field of Search ................................ 433/98, 28, 27, 433/215

[56] References Cited

U.S. PATENT DOCUMENTS

| | | | |
|---|---|---|---|
| 4,676,750 | 6/1987 | Mason | 433/98 X |
| 5,017,136 | 5/1991 | Gatti | 433/98 |
| 5,201,899 | 4/1993 | Austin, Jr. et al. | 433/98 |
| 5,538,423 | 7/1996 | Coss et al. | 433/98 X |

*Primary Examiner*—Nicholas D. Lucchesi
*Attorney, Agent, or Firm*—Townsend and Townsend and Crew

[57] ABSTRACT

The invention provides an exemplary modular dental system and methods for its use. In one exemplary embodiment, a dental system comprises a plurality of individual modules, with at least some of the modules including tool interfaces which may be coupled with one or more dental tools. Each of the modules includes a power interface, a communication interface, and a fluid interface to allow power, information, and fluids to be transferred between the modules when coupled together.

19 Claims, 7 Drawing Sheets

MODULAR DENTAL SYSTEM AND METHODS

CROSS-REFERENCE TO RELATED APPLICATIONS

This application is a continuation in part application and claims the benefit a U.S. provisional patent application No. 60/061,369, filed Oct. 8, 1997, the complete disclosure of which is herein incorporated by reference.

BACKGROUND OF THE INVENTION

This invention relates generally to the field of dentistry, and more specifically to the field of dental equipment. In a specific aspect, the invention relates to a modular dental system and methods for its use.

The dental industry has experienced significant changes over the last several years. For example, there has been increasing momentum for the dentist to expand his practice by offering additional services. However, offering of such services typically requires the acquisition of additional equipment to perform each specialized procedure. As one example, many dentists are now offering endodontic services. However, to perform such services, the dentist will need at least a set of endodontic files and may also require the use of an apex locator and special hand pieces to perform the procedure.

Presently, a dentist is required to purchase a separate piece of equipment for each new service. Unfortunately, the acquisition of specialized equipment to perform such additional procedures creates at least two problems. First, the dentist must find a location for each new piece of equipment. Second, each piece of additional equipment can be relatively expensive.

Hence, it would be desirable to provide systems and methods which would overcome or greatly reduce such problems. In particular, it would be desirable to provide systems and methods which would allow a dentist to expand his practice by adding additional procedures with minimal equipment and associated expenses. Such systems and methods should be easy to use to allow the dentist to rapidly become familiar with their mode of operation.

SUMMARY OF THE INVENTION

The invention provides exemplary dental systems and methods for their use. In one exemplary embodiment, a dental system includes a plurality of individual modules. At least some of the modules include tool interfaces to allow the modules to interface with one or more dental tools. Further, each of the modules includes a power interface, a communication interface and a fluid interface. In this way, power, information and fluids may be transferred between the modules when coupled together. Such a system is particularly advantageous in that a dentist may expand his practice to include additional procedures simply by purchasing another module and interfacing the module with the existing module. In this way, the required space for the new equipment is also minimized.

One of the modules preferably comprises a base module, which includes a power supply and a controller. In this way, the power to all of the modules of the system may be supplied from the base module. Similarly, the controller may be employed to communicate with the coupled modules over the communication interface. Conveniently, the power and control signals may be distributed and transmitted from the base module to each coupled module over the same electrical line. For example, the power interface and the communication interface may comprise a power distribution bus and a serial bus that is capacitatively coupled to the power distribution bus. In this way, the number of interfaces between the modules may be greatly reduced.

Each module preferably also includes an air interface and a fluid interface, such as a water interface. In this way, air and/or fluids, such as water, may be transmitted through each of the modules. In the event that a dental tool which is coupled to a specific module requires air or water, a line may be employed to tap into the main air or water line running through the module. In this manner, only one of the modules will need to be coupled to an air or water source.

In one particular aspect, the base module includes a motor and a coupler which is adapted to receive a dental tool. For example, a dental handpiece may be coupled to the base module, with operation of the motor being controlled by the controller. Optionally, the base module may include a computer interface, such as an RS-485 interface, to allow the base module to be coupled to an external computer.

In one particular aspect, one of the modules comprises an apex locator module which includes a coupler to allow an apex locator tool to be coupled to the apex locator module. In another aspect, one of the modules comprises an oral surgery/endodontic module to control operation of the motor in the base module. In this way, an oral surgery or endodontic tool may be coupled to the base module and be operated at a predetermined sequence as dictated by a controller in the oral surgery/endodontic module.

In another particular aspect, one of the modules comprises an irrigation control module which has a supply of liquid, to supply liquid to at least the base module through the fluid interface. In this way, any of the modules may receive a supply of liquid as supplied from the irrigation control module.

In still another aspect, one of the modules comprises a curing module which has a coupler to receive a curing light. One of the modules may also comprise a scaler module which includes a connecter to receive a scaler tool. Conveniently, liquid to the scaler tool may be provided from the irrigation module.

One particular advantage of utilizing the base module is that the modules which are coupled to the base module may also include a controller which may be programmed with a sequence of events associated with a different procedure. In this way, when coupled to the base module, a sequence may be transferred to the controller of the base module which will operate the motor and supply any air or liquid according to the procedure received from the coupled module. Conveniently, the base module may include a display panel which will display the relevant operating parameters as transferred by the coupled modules. Optionally, the base module may include a mode control which will allow the dentist to select one or more modes of operation as transferred from the coupled modules.

DESCRIPTION OF THE PREFERRED EMBODIMENT

Figure 1:
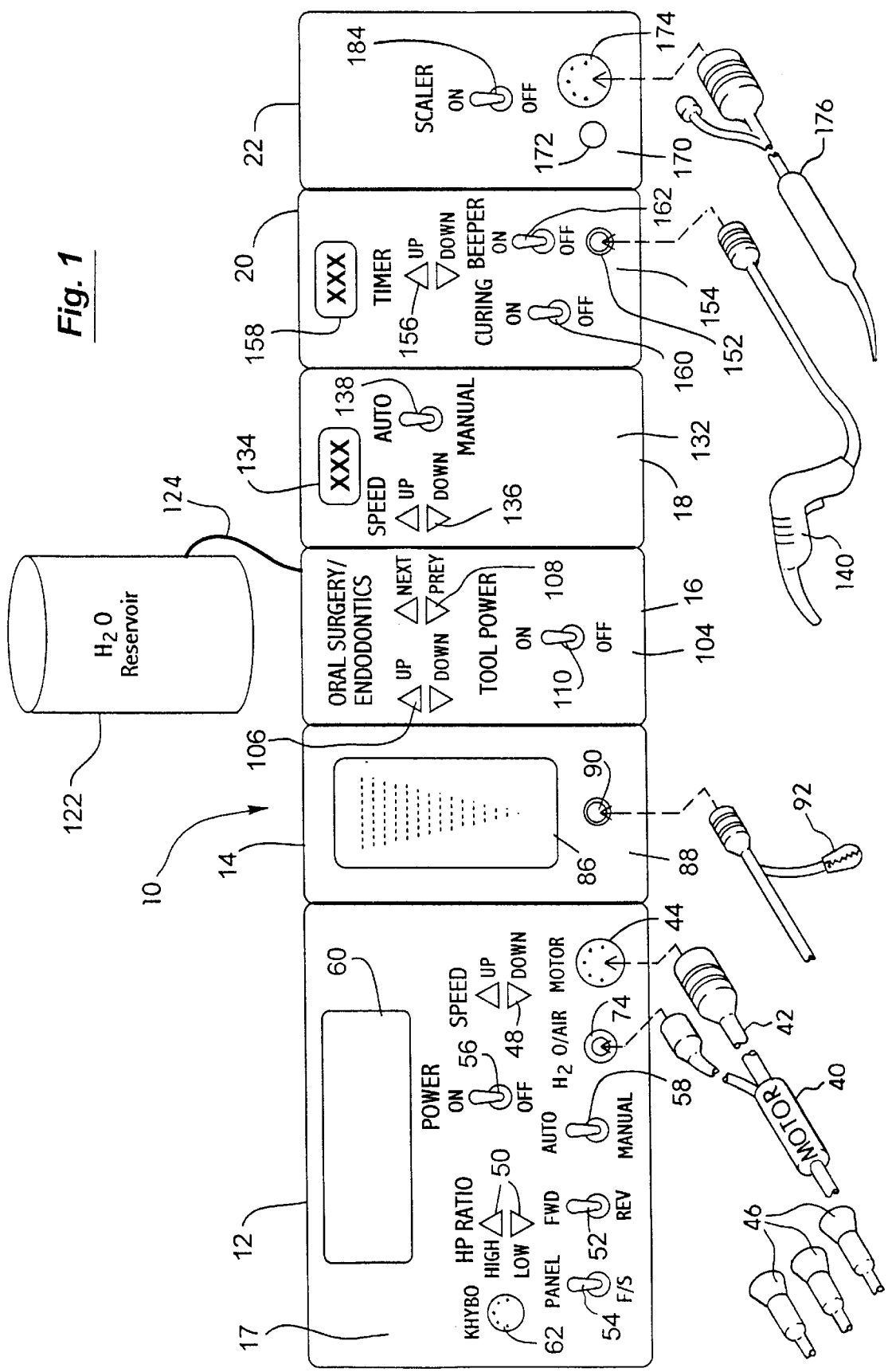
FIG. 1 is a front view of an exemplary modular dental system according to the invention.

The invention provides an exemplary modular dental system which is constructed of a plurality of individual modules. The modules are interconnectable with each other and include various interfaces to allow the modules to cooperate together. For example, each of the modules preferably includes a mechanical interface located at the side of the module to allow each of the modules to be mechanically coupled together. Further, each of the modules includes a power interface and a communication interface to allow power, commands and data to be transferred between the modules.

Each of the modules preferably includes an air and water interface to allow air and water to be transferred between the modules. Conveniently, the power interface and communication interface may be provided in a single line by employing a power distribution bus and a serial bus that is capacitatively coupled to the power distribution bus. In this way, power as well as data may be transferred over the same line which runs through each of the modules.

At least some of the modules are configured such that one or more dental tools may be coupled to the module. For example, the dental tools which may be coupled to the various modules include dental hand pieces, such as air/water syringes, apex locators, endodontic tools, oral surgery tools, scalars, curing lights, and the like. Dental tools which require the use of a motor for operation will preferably be connectible to the base module which includes a motor. Preferably the base module also includes a power supply and will be employed to provide power to the modules which are coupled to the base module. The base module preferably also includes a controller which is employed to operate the motor and which is employed to communicate with the various modules which are coupled to the base module. Optionally, the base module may include an RS-485 or similar interface to allow the base module to be connected to an external computer system, such as a conventional Pentium-type personal computer. The external personal computer may be employed to provide easier programming input as well as to monitor the status of all of the modules.

At least one of the modules will also include a controller. These controllers are preferably programmable so that the modules may be programmed according to predetermined operating procedures. In this manner, the base module may automatically, via resident programming, configure itself to accommodate each module that is connected to it. For instance, the base module preferably includes a display screen which will display the operating parameters for the coupled modules. In one example, an irrigation module may be connected to the base module which will detect the connection. The base module will then activate a specified line on the display to display the pertinent operating parameters of the irrigation module, e.g., the specified flow rate. Preferably, the base module will be configured to detect when a module has been coupled to it after the attached module is turned to an "on" position. When turned to the "on" position, the base module controller will communicate with the controller of the coupled module to determine the operating parameters specified in the controller of the coupled module. This information may optionally be displayed on the display of the base module as previously described. As one example, if an endodontic module is coupled to the base module and turned to the "on" position, the appropriate lines on the display of the base module will be displayed and the information from the endodontic module will be used to control the motor and hand piece which is coupled to the base module, the torque limits or speed limits, and the like. The base module is preferably programmed to address any potential conflicts that may arise if multiple modules are activated and have conflicting control procedures, e.g., one that controls torque and one that does not.

The power/communication interface and air/water interface are preferably provided on the sides of each module. In this way, the interfaces become embedded when the modules are mated together. By providing separate modules which interface in this manner, the storage space required for the system is greatly reduced. Moreover, by providing the power supply and main controller in the base module, the dentist may increase the number of offered procedures simply by purchasing a relatively inexpensive module and coupling the module to the base module. Further, the overall system is less expensive because only one power supply is needed for all of the modules.

Referring now to FIG. 1, an exemplary modular dental system 10 will be described. Central to system 10 is a base module 12 which provides power and control functions for the other modules in the system. Base module 12 is configured so that it may be coupled to one or more other modules which provide various features to the system, or may operate as a stand alone unit. As shown, base module 12 is coupled to an apex locator module 14, an oral surgery/endodontic module 16, an irrigation control module 18, a curing module 20, and a scalar module 22. It will be appreciated that various combinations of such modules may be coupled to base module 12. Further, it will be appreciated that the order in which the modules are coupled to base module 12 is not important. Preferably, each of the modules includes a mechanical interface to allow the modules to conveniently be coupled together as shown.

Figure 2:
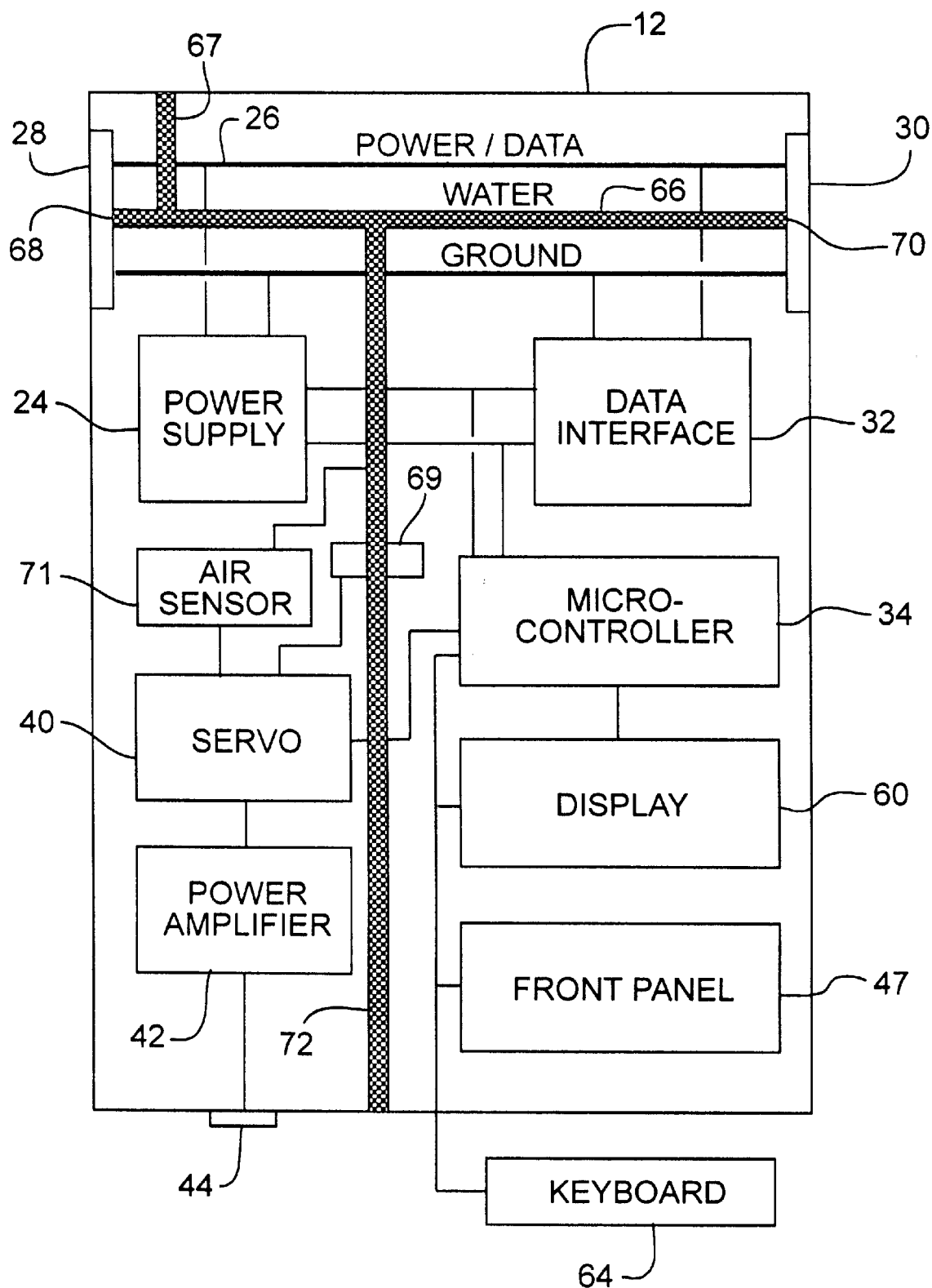
FIG. 2 is a schematic diagram of a base module of the system of FIG. 1.

Referring also now to FIG. 2, construction of base module 12 will be described in greater detail. Base module 12 includes a power supply 24 which provides power to base module 12 as well as to the other modules coupled to base module 12. Power supply 24 converts a standard AC input into a 24 VDC distributed power bus for system 10. More specifically, a power/data line 26 is coupled to power supply 24 and serves as a power bus to distribute power to each of the connected modules. Conveniently, module 12 includes power/data interfaces 28 and 30 which allow power/data line 26 to be coupled to the power/data line of a connecting module. Also coupled to both power supply 24 and power/data line 26 is a data interface 32. Coupled to data interface 32 is a controller 34. With such a configuration, data may be transferred between the modules over power/data line 26. Such a configuration is particularly advantageous in that both power and data may be transferred over the same line to minimize the amount of electrical interfaces between the modules. Data interface 32 preferably comprises a serial bus, such as a CAN bus or other buses as are known in the art, that is capacitatively coupled to power/data line 26.

Controller 34 is employed to control the status display, monitor various switches, control a drill motor, and provide intelligence for the attached modules. For example, controller 34 is coupled to a servo 36 and to a power amplifier 38 which controls a motor 40 of a drill 42. The torque of motor 40 is detected by measuring the motor current. The motor speed is inferred by measuring the motor back voltage. Further, the motor speed is controlled in response to requests from various controls on base module 12 as well as from optional modules as described hereinafter. Conveniently, a motor interface 44 is provided on base module 12 to allow drill 42 to be coupled to base module 12. Optionally, various handpieces 46 may be provided in connection with drill 42 to facilitate various procedures. For example, such handpieces can include laboratory type handpieces, contra angle type handpieces, speed reducers, speed increasers, and the like.

Base module 12 includes a front panel 47 which includes the various switches and controls for operating base module 12. The speed of motor 40 may be manually controlled by speed controls 48 on base module 12. Speed controls 48 are coupled to controller 34 to allow the speed to be increased or decreased by pressing the up or down control. A handpiece ratio control 50 is provided on base module 12 to indicate the gear ration of the handpiece connected to motor 40. The direction control 52 is also provided on base module 12 to control the direction of rotation of motor 40. A panel/footswitch control 54 allows the dentist to operate motor 40 from the front panel of base module 12 or from a separate foot switch (not shown). Base module 12 further includes a power switch 56 which allows power to be supplied to power supply 24 when turned to the on position.

Another feature of base module 12 is that it includes an auto/manual control 58 which allows drill 42 to be operated either manually or automatically by one or more programs which is stored in controller 34. For example, when in the manual position, the speed may be manually adjusted using control 48. When placed in the automatic mode, drill 42 will be operated using preprogrammed procedures entered into controller 34. Although not shown, base module 12 may include a mode control switch which allows a dentist to scroll through various preprogrammed modes of operation.

Conveniently, base module 12 includes a display 60 which is coupled to controller 34 and provides alphanumeric feedback to the operator of the state of the system. Merely by way of example, display 60 may display the speed, handpiece ratio, direction of operation of motor, whether base module 12 is in automatic or manual mode, and the like. Conveniently, base module 12 includes a keyboard interface 62 to allow a keyboard to be coupled to base module 12. Keyboard 64 may be used to program controller 34 as well as in assisting in oral surgery procedures as described hereinafter. Although not shown, base module 12 may optionally include an RS-485 interface to allow base module 12 to be coupled to an external computer.

Another feature of base module 12 is that it includes a fluid line 66 which passes through base module 12. A pair of fluid interfaces 68 and 70 are provided to allow various fluids to pass through base module 12. Fluid line 66 may be employed to transport fluids such as water, air, and the like. If both water and air are to be used, two separate lines may optionally be employed. Coupled to fluid line 66 is a line 72 which terminates in a water/air connector 74. In this way, air or water may be provided to drill 42.

System 10 is constructed such that it may receive fluids, such as water, and gases, such as air, from one of two sources. In one way, base module 12 may include an office air/water interface 67 which allows base module 12 to receive fluids and air from an existing air/fluid system within the dental office. Interface 67 preferably comprises a standard hose connector which may be coupled with the air/fluid hose of standard air driven handpieces. Interface 67 is coupled to fluid line 66, and a valve 69 and sensor 71 are provided so that when the hose is connected to interface 67, base module 12 will know that it is coupled to an air or fluid source. When the footswitch of base module 12 is operated, valve 69 is opened to allow the fluid to be supplied to drill 42. In the second way, fluids or air may be provided to base module 12 via irrigation module 18, as described hereinafter.

Optionally, motor interface 44 may include a mechanism for detecting the type of dental tool which is coupled to base module 12. In this way, controller 34 may configure base unit 12 to operate according to the coupled dental tool.

Figure 3:
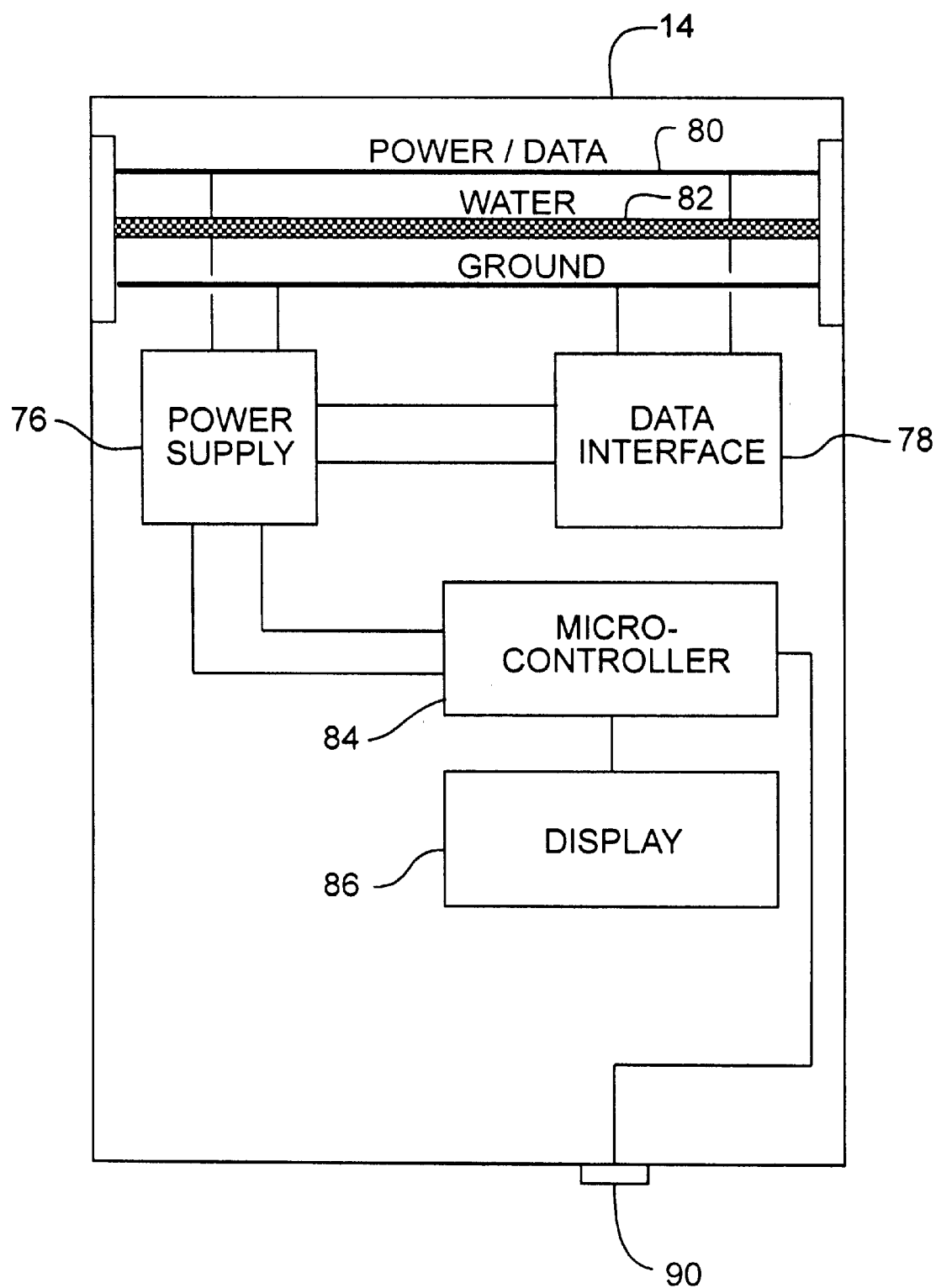
FIG. 3 is a schematic diagram of an apex locator module of the system of FIG. 1.

Referring now to FIGS. 1 and 3, apex locator module 14 will be described in greater detail. Apex locator module 14 includes a power supply 76 and a data interface 78 which are coupled to a power/data line 80. In this way, power and data from base module 12 may be transferred over power/data line 80 to power supply 76 and data interface 78 when module 14 is coupled to module 12. A fluid line 82 passes through module 14 to allow various fluids to be transferred through module 14 so that the fluid will be accessible to other modules. Module 14 further includes a controller 84 which provides intelligence for module 14. Controller 84 is coupled to a display 86 on a front panel 88 of module 14. Module 14 includes an apex tool connecter 90 to allow an apex tool 92 to be coupled to module 14. The sensor input from apex tool 92 is transferred to controller 84 which displays the position on display 86. Display 86 preferably displays the position of the tool with respect to the apex on a two-dimensional graphical display with audio indication at selected positions.

Figure 4:
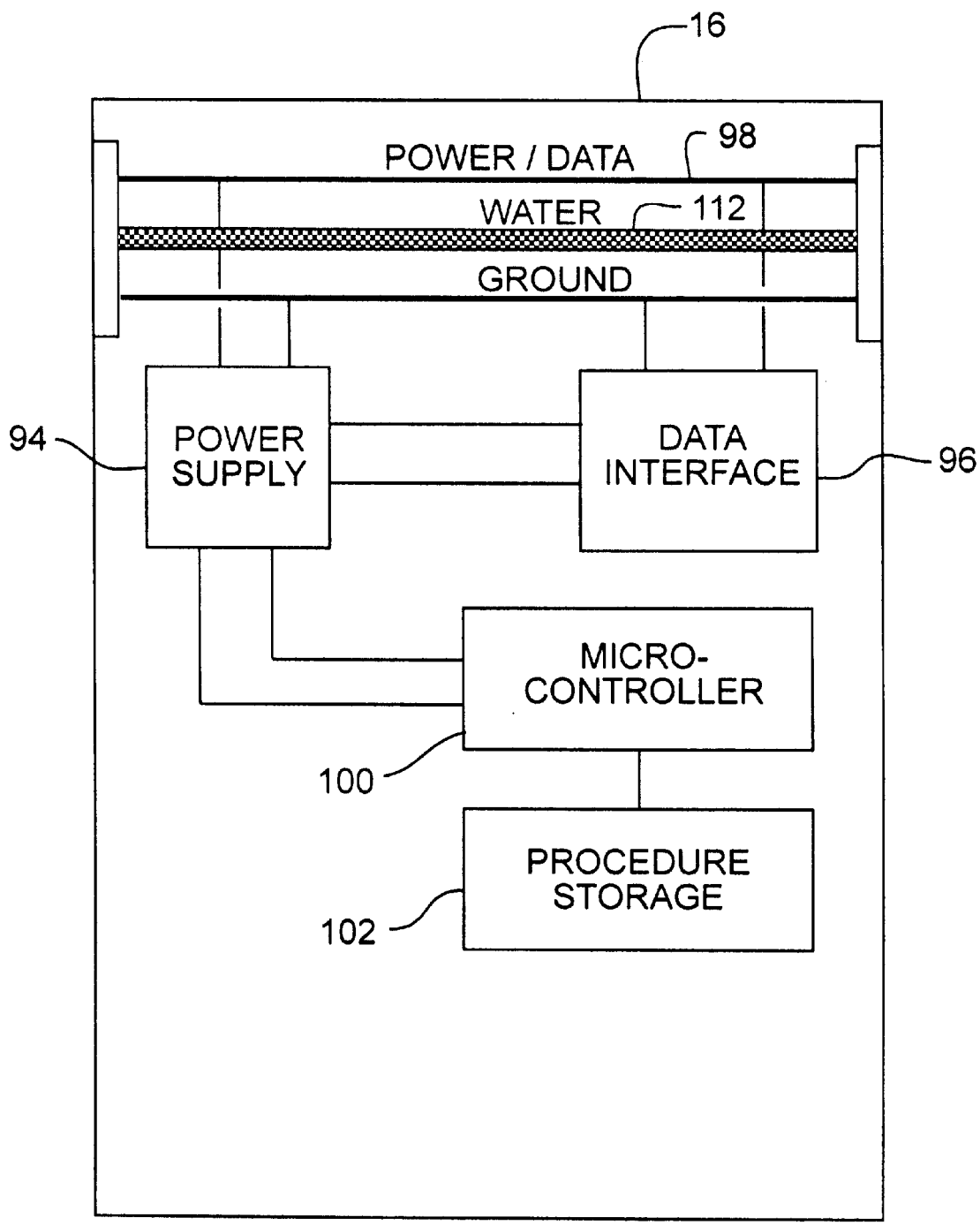
FIG. 4 is a schematic diagram of an oral surgery/endodontic module of the system of FIG. 1.

Referring to FIGS. 1 and 4, oral surgery/endodontic module 16 will be described in greater detail. Module 16 is preferably employed to control operation of drill 42. Also, when used in connection with irrigation control module 18, module 16 is employed to control the operation of water and air to drill 42. Module 16 includes a power supply 94 and a data interface 96 which are coupled to a power/data line 98 similar to module 14. A controller line 100 is coupled to power supply 94 and data interface 96 and provides intelligence for module 16. Module 16 further includes a procedure storage unit 102 which is coupled to controller 100. In this way, various procedures may be programmed into controller 100 and stored in procedure storage unit 102. When module 16 is coupled to module 12, any one of the stored procedures may be accessed by module 12 to allow drill 42 to be operated according to the stored procedure. Conveniently, controller 100 may be programmed using keyboard 64 (see FIG. 2). Module 12 also preferably includes a program set control (not shown) which allows for programming of controller 100. Further, display 60 may be employed to display the various parameters which may be programmed into controller 100. For example, controller 100 may be programmed to include parameters which control operation of motor speed, motor torque, and water flow. Various combinations of these parameters may be stored in procedure storage unit 102 and transferred to base module 12 when needed as previously described.

Conveniently, module 16 further includes a front panel 104 with controls for controlling the torque of motor 40 (instead of using keyboard 64). More specifically, front panel 104 includes an up/down control 106 to increase or decrease the torque of motor 40. A next/previous control 108 is adjacent up/down control 106 and is provided to allow for stepping through an automatic program. Controls 106 and 108 may also be employed to manually control the operating parameters of drill 42.

Front panel 104 further includes an on/off switch 110. When module 16 is coupled to base module 12, and switch 110 is in the off position, no programming procedures stored in unit 102 will be transferred to base module 12. However, when switch 110 is turned to the on position, appropriate lines on display 60 relating to the parameters stored in module 16 will be actively displayed. The operator may then select a desired procedure which is stored in unit 102. Module 12 will then operate drill 42 according to the torque limits, water flow, and the like, provided by the launched procedure.

Figure 5:
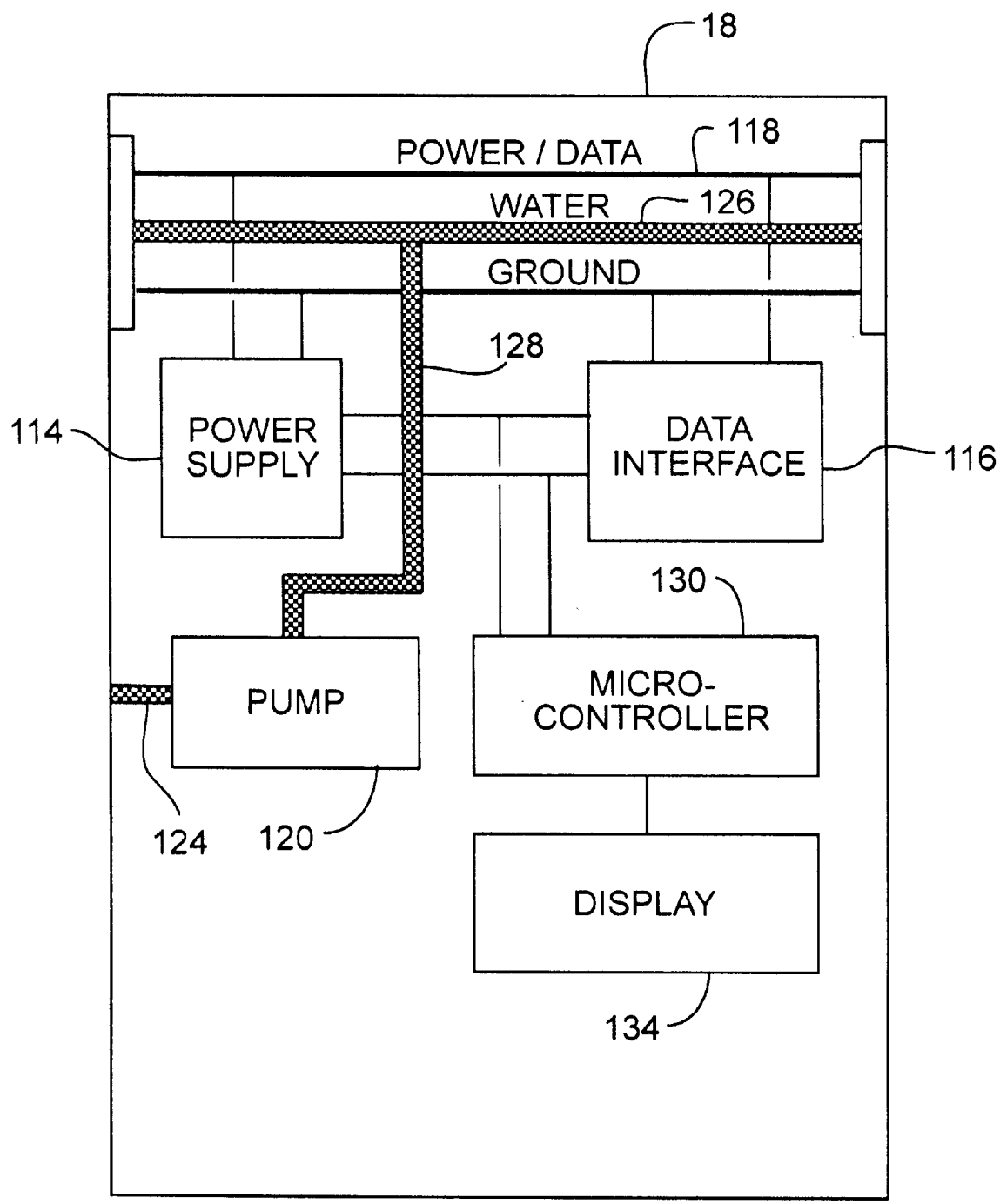
FIG. 5 is a schematic diagram of an irrigation module of the system of FIG. 1.

Module 16 further includes a fluid line 112 which allows fluids to flow through module 16. Module 16 is preferably coupled to irrigation control module 18 as illustrated schematically in FIG. 5. Module 18 includes a power supply 114 and a data interface 116 which are coupled to a power/data line 118 similar to previous modules. Irrigation control module 18 also includes a pump 120 which is in fluid communication with a fluid reservoir 122 (see FIG. 1) by a line 124. Pump 120 is also coupled to a fluid line 126 which passes through module 18 by a line 128. In this way, irrigation control module 18 may be employed to transfer fluids between the various modules. It will be appreciated that various fluid movement schemes may be employed to move the fluids, including peristaltic pumps and other types of pumps. Although not shown, module 18 may be coupled to a pressurized gas source to allow various pressurized gases to be transferred between the modules.

Module 18 further includes a controller 130 which communicates with the controller 34 of base unit 12 over power/data line 118. For example, the capacity of reservoir 122 may be stored in controller 130 so that when module 18 is coupled to module 12, the capacity will be displayed on display 60. As fluids are depleted from reservoir 122, the remaining fluid within reservoir 122 may be displayed on display 60. Controller 34 may also be configured to communicate with controller 130 to monitor the output of pump 120 to verify that an appropriate output is being delivered.

Module 18 includes a front panel 132 having a display 134 which may also be employed to show various parameters of the fluid, such as the flow rate. Front panel 132 further includes a speed control 136 which allows a user to manually adjust the flow rate of the fluid. An automatic/manual switch 138 is also provided to allow module 16 to be operated in either a manual mode or an automatic mode. In the manual mode, controls 136 are used to adjust the flow rate. In the automatic mode, controller 130 will be employed to transfer preprogrammed parameters to controller 34 of base module 12. As with the other modules, when irrigation control module 18 is coupled to base module 12, base module 12 activates a specified line or lines on display 60 to display the pertinent operating parameters that are transferred from controller 130. For example, a preset flow rate may be transferred to base module 12 and displayed on display 60 when module 18 is coupled to module 12. Base module 12 includes resident programming that allows display 60 to be appropriately configured for each module that is coupled to base module 12.

Figure 6:
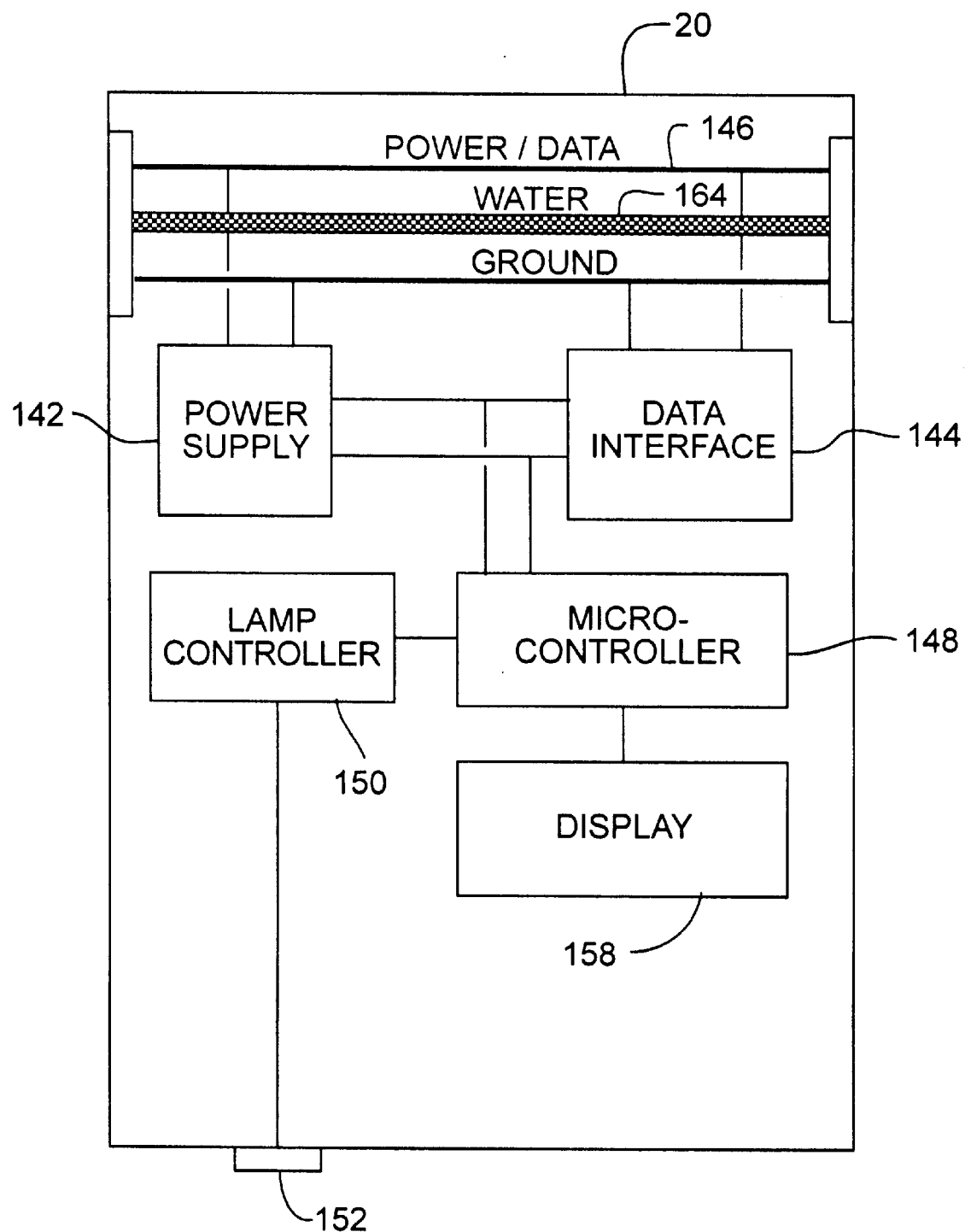
FIG. 6 is a schematic diagram of a curing module at the system of FIG. 1.

Referring now to FIGS. 1 and 6, construction of curing module 20 will be described in greater detail. Curing module 20 is employed to control an ultraviolet light in a curing tool 140 which in turn is used to cure light sensitive compounds. Module 20 includes a power supply 142 and a data interface 144 which are coupled to a power/data line 146 similar to other modules. Module 20 further includes a controller 148 to allow module 20 to communicate with base module 12 in a manner similar to other modules previously described.

Controller 148 is also coupled to a lamp controller 150 which is coupled to a connecter 152. As best shown in FIG. 1, module 20 includes a front panel 154 which includes connecter 152. In this way, tool 140 may be coupled to connector 152. Front panel 154 also includes a timer control 156 and a display 158. In this way, the time at which the ultraviolet light will be actuated may be set by controls 156 and displayed on display 158.

Front panel 154 further includes an on/off switch 160 which allows module 120 to be turned to an on position so that it may communicate with base module 12. Base module 12 may be employed to program the power level supplied to the curing light by lamp controller 150. Optionally, a beeper switch 162 is provided on front panel 154 and may be turned to the on position to provide an audible tone for every selected time interval that is displayed on display 158. In this way, a tone is provided to give audio feedback on the amount of elapsed time.

Optionally, connector 152 may be configured to detect when different types of lamp tools are connected to module 20. Also, a fluid line 164 passes through module 20 to allow various fluids to be distributed to other modules which are connected to module 20 in a manner similar to previous embodiments.

Figure 7:
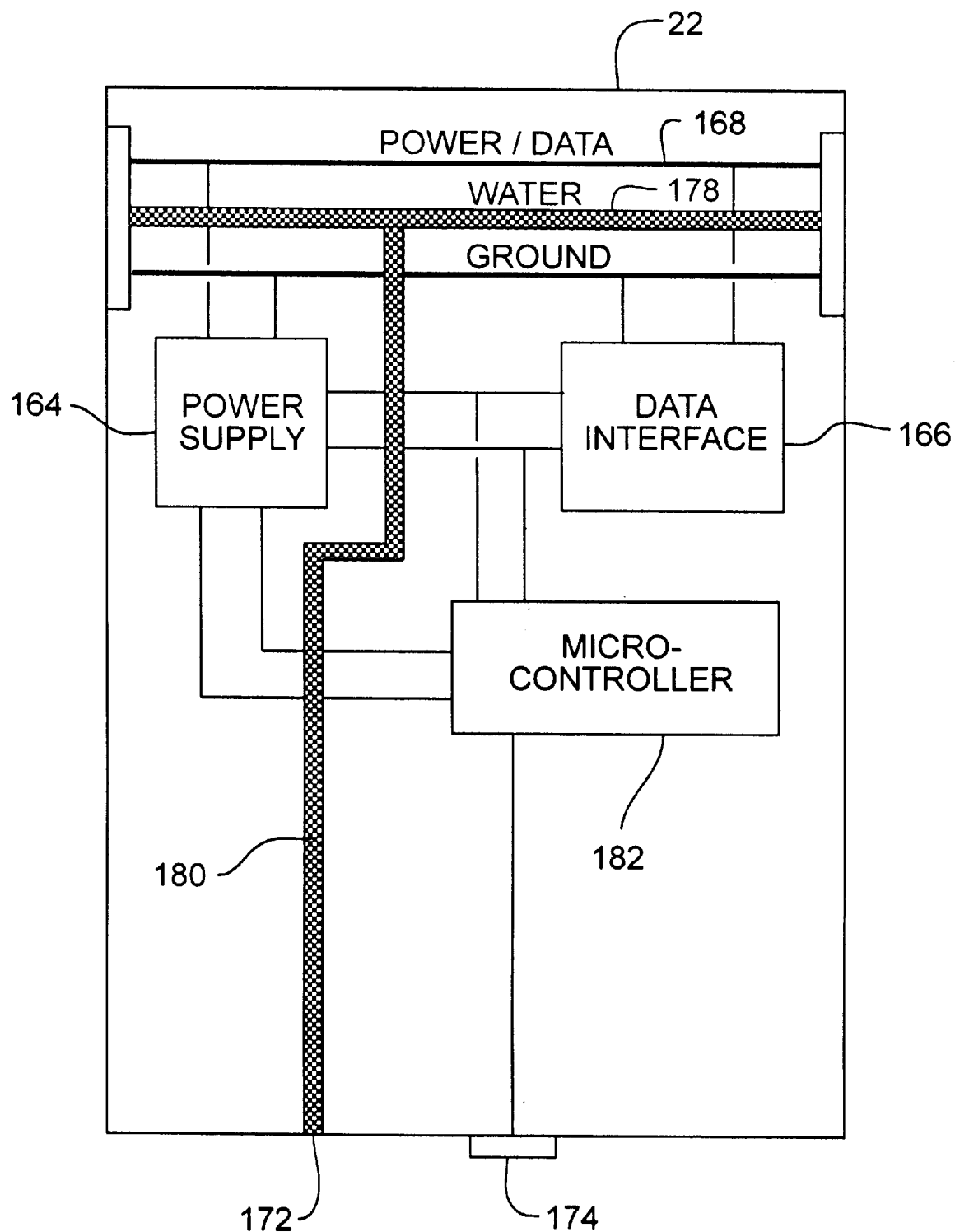
FIG. 7 is a schematic diagram of a scalar module at the system of FIG. 1.

Referring now to FIGS. 1 and 7, construction of scalar module 22 will be described in great detail. Similar to the other modules, scaler module 122 includes a power supply 164 and a data interface 166 which are coupled to a power/data line 168 to allow power and data to be transferred between module 22 and base module 12. Module 122 further includes a front panel 170 having connectors 172 and 174 to which a scaling tool 176 may be coupled. A fluid line 178 passes through module 22 and is coupled to another fluid line 180 which provides water to tool 176 through connector 172. Connecter 174 is coupled to a controller 182 which is employed to operate tool 176. Front panel 170 further includes an on/off switch 184 which allows module 22 to interface with module 12 when turned to the on position. Further, module 12 may include resident programming which will operate scaling tool 176 when switch 184 is turned to the on position. In this way, the control of module 22 may be accomplished using the components in base module 12 similar to the other embodiments. Optionally, tool 176 may be operated with a foot control that is coupled to the system.

Although system 10 has been described with specific modules, it will be appreciated that essentially any type of module that assists the dentist may be coupled to the system, including modules which operate tools yet to be developed. For example, modules which operate dental tools, laboratory tools, orthodontic tools, periodontic tools, and the like may be included. Further, it will be appreciated that the modules may be arranged in essentially any type of arrangement and combination as required by a particular dentist.

The invention has now been described in detail for purposes of clarity and understanding. However, it will be appreciated that certain changes and modifications may be practiced within the scope of the appended claims.

What is claimed is:

1. A dental system comprising:
   a plurality of individual modules, wherein at least some of the modules include tool interfaces which are adapted to interface with one or more dental tools, wherein each of the modules includes a power interface, a communication interface and a fluid interface to allow power, information, and fluids to be transferred between the modules when coupled together, wherein one of the modules comprises a base module having a power supply and a controller, wherein power to the modules coupled to the base module is supplied by the power supply over the power interface, and wherein the controller is configured to communicate with the coupled modules over the communication interface.

2. A system as in claim 1, wherein the power interface and the communication interface comprise a power distribution bus and a serial bus capacitively coupled to the power distribution bus.

3. A system as in claim 1, wherein the dental tools are selected from the group of tools consisting of dental handpieces, apex locators, endodontic tools, oral surgery tools, scalars, and curing lights.

4. A system as in claim 1, wherein each module includes a water interface and a gas interface.

5. A system as in claim 1, wherein the base module includes a motor and a coupler which is adapted to receive a dental tool, and wherein operation of the motor is controlled by the controller.

6. A system as in claim 1, wherein the base module includes a computer interface to allow base module to be coupled to an external computer.

7. A system as in claim 1, wherein one of the modules comprises an apex locator module having a coupler which is adapted to receive an apex locator tool.

8. A system as in claim 1, wherein one of the modules comprises an oral surgery/endodontic module to control operation of the motor in the base module.

9. A system as in claim 8, wherein one of the modules comprises an irrigation control module having a supply of liquid to supply liquid to at least the base module through the fluid interface.

10. A system as in claim 9, wherein the base module includes an external connector which is adapted to be coupled to a dental office air/fluid system so that fluids or gases may be supplied to the base module from the dental office air/fluid system or from the irrigation control module.

11. A system as in claim 1, wherein one of the modules comprises a curing module having a coupler which is adapted to receiving a curing light.

12. A system as in claim 1, wherein one of the modules comprises a scalar module having a connector which is adapted to receive a scalar tool.

13. A method for performing a dental procedure, comprising:
providing a base module having a power supply and a controller;
coupling an irrigation module to the base module, wherein power to the irrigation module is provided by the base module;
coupling a dental tool to the base module; and
operating the dental tool while supplying a fluid to the dental tool from the irrigation module based at least in part on commands received by the irrigation module from the controller.

14. A method as in claim 13, further comprising controlling actuation of the flow of the liquid and the flow rate of the liquid with the irrigation module.

15. A method as in claim 13, further comprising coupling an apex locator module to the base module, coupling an apex locator tool to the apex locator module, and supplying power to the apex locator tool from the base module.

16. A method as in claim 13, further comprising coupling an oral surgery/endodontic module to the base module, coupling an oral surgery tool to the base module, and controlling operation of the motor in the base module with the oral surgery/endodontic module.

17. A method as in claim 13, further comprising coupling a curing module to the base module, coupling a curing light to the curing module, and supplying power to the curing light from the base module.

18. A method as in claim 13, further comprising coupling a scalar module to the base module, coupling a scalar tool to the scalar module, supplying power to the scalar tool from the base module, and supply liquid to the scalar tool from the irrigation module.

19. A method for performing a dental procedure, comprising:
providing a base module having a power supply and a controller;
coupling an accessory module to the base module, wherein power to the accessory module is provided by the base module;
coupling a dental tool to the base module; and
operating the dental tool based on commands transferred to the base module from the accessory module.

* * * * *